(12) United States Patent
Kinyon

(10) Patent No.: US 9,926,116 B2
(45) Date of Patent: Mar. 27, 2018

(54) PACKAGING FOR MEDICAL ARTICLES SUCH AS A SIZE VARYING SERIES OF ORTHOPEDIC IMPLANTS

(71) Applicant: Tad R. Kinyon, Elysian, MN (US)

(72) Inventor: Tad R. Kinyon, Elysian, MN (US)

(73) Assignee: Bemis Company, Inc., Neenah, WI (US)

( * ) Notice: Subject to any disclaimer, the term of this patent is extended or adjusted under 35 U.S.C. 154(b) by 716 days.

(21) Appl. No.: 14/391,119

(22) PCT Filed: Apr. 23, 2013

(86) PCT No.: PCT/US2013/037767
§ 371 (c)(1),
(2) Date: Oct. 7, 2014

(87) PCT Pub. No.: WO2013/163160
PCT Pub. Date: Oct. 31, 2013

(65) Prior Publication Data
US 2015/0076023 A1    Mar. 19, 2015

Related U.S. Application Data

(63) Continuation-in-part of application No. 13/457,798, filed on Apr. 27, 2012, now abandoned.

(51) Int. Cl.
*A61B 17/06* (2006.01)
*A61B 19/02* (2006.01)
(Continued)

(52) U.S. Cl.
CPC ............ *B65D 51/00* (2013.01); *A61F 2/0095* (2013.01); *A61F 2/36* (2013.01)

(58) Field of Classification Search
CPC ........ B65D 85/06; B65D 85/30; B65D 51/00; A61F 2/0095; A61F 2/36; A61B 19/0271
(Continued)

(56) References Cited

U.S. PATENT DOCUMENTS 3,353,664 A    11/1967  Armentrout
3,786,982 A *   1/1974  Rakes ...................... B65D 1/26
                                                             220/324
(Continued)

FOREIGN PATENT DOCUMENTS

EP    0523895 A1   1/1993
NL    6708222 A    12/1968

*Primary Examiner* — J. Gregory Pickett
*Assistant Examiner* — Rafael Ortiz
(74) *Attorney, Agent, or Firm* — Lynn M. Nett

(57) ABSTRACT

Packaging which can accommodate medical articles such as a series of orthopedic implants e.g. femoral stem components for prosthetic hip joints which have a dimension which varies minimally across the series but which vary considerably in overall size. The packaging is designed to minimize the travel of any member of the series packaged therein such that all the packaged components in the series can pass the standard handling and shipping tests typically used by the manufacturers of medical articles such as implants and preferably comprises two thermoformed tray components which each carry three types of cavities which are interconnected and designed to be assembled with their cavities facing each other to contain the lower stem, body and angled shaft of the stem component, respectively, with the cavities for the lower stem and the body cooperating to capture a minimally varying dimension of the series.

6 Claims, 3 Drawing Sheets

(51) Int. Cl.
*A61L 15/00* (2006.01)
*B65D 51/00* (2006.01)
*A61F 2/00* (2006.01)
*A61F 2/36* (2006.01)

(58) Field of Classification Search
USPC ....... 206/363, 773, 774, 470, 562, 780, 349, 206/438, 63.3, 734, 736, 747, 748, 749, 206/306, 443, 564, 557, 563; 220/4.21–4.27, 4.29
See application file for complete search history.

(56) References Cited

U.S. PATENT DOCUMENTS

| | | | |
|---|---|---|---|
| 4,512,474 A | 4/1985 | Harding | |
| 4,697,703 A | 10/1987 | Will | |
| 4,921,096 A | 5/1990 | McFarlane | |
| 4,951,812 A * | 8/1990 | Chen | B25H 3/023 190/16 |
| 5,193,679 A * | 3/1993 | White | A61F 2/0095 206/363 |
| 5,379,895 A | 1/1995 | Foslien | |
| 5,392,909 A | 2/1995 | Hackett | |
| 5,474,179 A | 12/1995 | Iosif | |
| 5,494,162 A | 2/1996 | Treace et al. | |
| 5,772,031 A | 6/1998 | Landis | |
| 5,788,105 A * | 8/1998 | Foos | B65D 43/162 206/1.5 |
| 5,842,567 A | 12/1998 | Rowe et al. | |
| 6,012,580 A | 1/2000 | Peters et al. | |
| 6,330,945 B1 | 12/2001 | Reimer | |
| 6,561,805 B2 | 5/2003 | Kumar | |
| 7,073,680 B2 | 7/2006 | Boback | |
| 7,118,003 B2 | 10/2006 | Sellari et al. | |
| 7,316,318 B1 | 1/2008 | Rosten et al. | |
| 7,648,030 B2 | 1/2010 | Landis | |
| 7,931,148 B2 | 4/2011 | Hansen et al. | |
| 2002/0104770 A1 | 8/2002 | Shapeton et al. | |
| 2003/0148124 A1 | 8/2003 | Yamada et al. | |
| 2005/0098460 A1 | 5/2005 | Smith et al. | |
| 2007/0102317 A1 | 5/2007 | Crawford et al. | |
| 2007/0295620 A1 | 12/2007 | Collet et al. | |
| 2011/0036736 A1 * | 2/2011 | Knowlton | A61B 19/026 206/438 |
| 2011/0155592 A1 | 6/2011 | Liccardo et al. | |

* cited by examiner

PACKAGING FOR MEDICAL ARTICLES SUCH AS A SIZE VARYING SERIES OF ORTHOPEDIC IMPLANTS

BACKGROUND OF THE INVENTION

The packaging of the femoral stem component used in the orthopedic hip arthroplasty procedure has traditionally involved the use of inserts to stabilize the stem component within the package and these inserts have been tailored to the size of a particular stem component. Stem components are currently available in a substantial number of sizes with some manufacturers offering as many as ten sizes in order to better meet the needs of individual patients.

The traditional packaging of sterile medical devices such as implants including stem components has involved a system of an inner tray within an outer tray. Each tray is typically an open mouthed cavity with a peripheral rim to which a film is adhesively adhered to create a sealed package. The outer tray simply contains the inner tray which in turn contains the medical device, commonly stabilized within the tray with closed cell foam pieces. The pieces of foam are commonly selected to have configurations adapted to the particular device being packaged. Thus in the case of stem components different pieces of foam are required in progressing across the size range of such components. The two tray system provides some assurance that if the integrity of the outer tray is breached in shipping and handling, the steriiity of the packaged medical device is preserved by the inner tray.

This two tray system has some disadvantages. The foam used for stabilization within the inner tray is friable and, particularly with orthopedic implants with roughened surfaces to enhance bonding to living tissue, typically bone, it has been observed to abrade, creating a particulate contaminate. In addition, because the peripheral rim of the inner tray typically carries residual adhesive after the removal of the lid stock, it may not be placed on the surgical tray adjacent to the surgeon implanting the device. Consequently, the medical device must be fully removed from its protective packaging well before its use and is thus exposed to damage and being splashed with bodily fluids and tissue while awaiting implantation.

Thus there are benefits to be gained from a packaging approach in which a single package can be used across the size range of at least a single line of femoral stem components of a given design or from a single manufacturer. There are further benefits to be obtained from a complete package which can be removed from an inner tray and placed on a surgical tray thus providing protection for the packaged component until it is used and providing a convenient manner of presenting the component to the surgical team.

SUMMARY OF THE INVENTION

The present invention involves a package which is adapted to securely hold medical articles such as medical instruments or implants e.g. orthopedic implants such as any of a series of femoral stem components of artificial hip joints which have a dimension which does not vary greatly over a significant size range. This package is configured to provide a clearance which captures and closely approximates a minimally varying dimension of a medical article.

In the present invention a rigid, synthetic e.g. thermoplastic polymer package is provided having (A) a rigid base and (B) a cover having at least two compartments connected by a connecting hinge. The base and cover may also be connected by a peripheral hinge. The first compartment has a first interior surface and opposing first exterior surface where the first interior surface has one or more cavities whereby this first interior surface is adapted for movement restraining contact with a first portion of a medical article which has a fixed or minimally varying dimension. The second compartment has a second interior surface and opposing second exterior surface where the second interior surface has one or more cavities whereby this second interior surface is adapted for contact, preferably movement restraining contact, with a second portion of a medical article. The connecting hinge connects the first and second compartments to each other and provides for manual movement of the first compartment relative to the position of the second compartment to rotate the first interior surface away from the second interior surface and the opposite rotational movement is restricted or prevented e.g. the first interior surface cannot be rotated to cover the second interior surface.

One convenient way to provide the aforementioned clearance which captures and closely approximates a minimally varying dimension in a package for an orthopedic implant such as a hip implant is to provide a fairly flat rectangular package with three distinct but interconnected cavities, each of which accommodates one of the three distinct elements of a femoral stem component. In this regard, the typical stem component is comprised of a lower stem which is a long generally cylindrical portion adapted to be inserted into a femur, an angled shaft which is a short cylindrical portion adapted to be inserted into the femoral head or ball and a body which is a transition portion, also adapted to be inserted into the femur, which connects the short and long cylindrical portions. One edge of this body is typically just an extension of one edge of the lower stem and the other edge proceeds outward at an acute angle from the main axis of the lower stem. The angled shaft then extends outward from the end of the body distal from the lower stem at an acute angle to the main axis of the lower stem which is typically greater than the acute angle between the one edge of body and said axis. These three portions typically have about the same thickness such that they all extend about the same distance in a z direction where x and y directions extend along the length and width of the femoral stem component. In a preferred embodiment the largest member of the series femoral stem components for which the package is adapted just fits within the package with smaller members fitting in with some overall clearance.

One convenient approach is a package having a first compartment having first and second cavities connected by an integrally formed hinge to a second compartment having a cavity. In this approach the capturing clearance is provided by the cooperation of the second compartment's cavity adapted to contain the lower stem and the first compartment's cavity adapted to contain the body. In this approach, a communication port between these two cavities is sized to prevent the entrance of the body from the first compartment into the second compartment's cavity for the lower stem; and in the first compartment a wall of the first cavity adapted to contain the body distal from this port limits the motion of the body toward the second cavity adapted to contain the angled shaft. For this approach the cavities for the lower stem in the second compartment and the angled shaft in the first compartment may readily accommodate the full size range of the series with a significantly greater clearance. In a preferred embodiment, this distal wall of the body cavity is at an obtuse angle to the main axis of the lower stem cavity of the package. In a particularly preferred embodiment the body cavity has a wall which is a continuation of a wall of the lower stem cavity and the obtuse wall begins at the end of this continuation wall distal from the port between the lower stem cavity and the body cavity. In a particularly preferred embodiment the package is provided with two sets of cavities to accommodate the angled shaft and lower stem parts of the femoral stem component with both sets of cavities communicating with a common cavity for accommodating the body part. In an especially preferred version of this approach this common cavity for accommodating the body has two walk parallel to the main axis of the lower stem cavities, which are themselves parallel to each other, with each wall terminating at its end distal to the ports communicating with the lower stem cavities in an obtuse wall which in turn extends to one of the ports communicating with one of the cavities for accommodating the angled shaft.

One convenient approach to creating a package for a series of orthopedic implants such as femoral stem components is to create two flat generally rectangular tray components which are mirror images of each other, with each carrying one half of the three portions to adapted accommodate the lower stem, the body and the angled shaft, respectively, of the femoral stem component. These tray components are provided with means which reversibly lock them together so as to create the three communicating cavities which will accommodate the series of femoral stem components. In a preferred embodiment, each tray component is provided with a hinge located at approximately the juncture between the cavity for the lower stem and the cavity for the body which extends across the width of the tray component to define an upper tray section and a lower tray section. The two mating lower tray sections are provided with locking means which function to hold them together and the two mating upper tray sections are provided with locking means which function to reversibly hold them together. The two hinges and the reversible upper tray section locking means function to allow the two upper tray sections to be rotated away from each other. In an especially preferred embodiment the two tray components each carry two cavities for the lower stem and two cavities for the angled shaft and the two oblique walls discussed above.

In another approach, mating trays need not be utilized, but instead a generally flat rigid base is employed with a cover similar to the tray above but having deeper cavities in its first and second compartments. This base and cover may be either separate components or they themselves may be connected by a hinge at one of the peripheral edges of the cover.

DETAILED DESCRIPTION OF THE INVENTION

Figure 1:
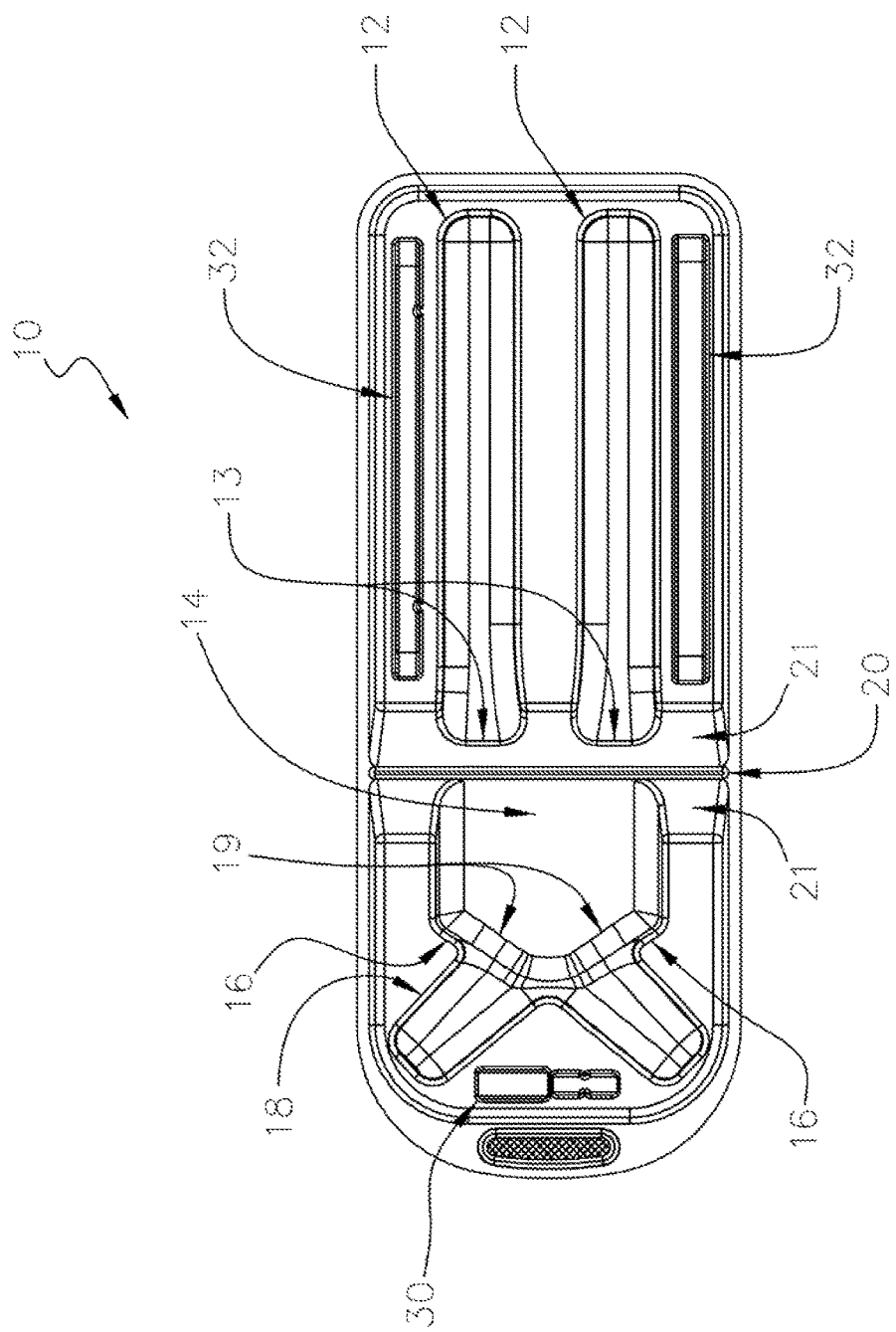
FIG. 1 is a plan view of one of the two tray components 10 which may be a cover or base showing its longer hemi-tubular cavities 12, the ports 13 leading from the cavities 12 to its transition cavity 14, the oblique walls 16 of its transition cavity 14, the ports 19 leading from cavity 14 to its shorter hemi-tubular cavities 18, its hinge 20, its reversible upper tray section locking means 30 and its reversible lower tray section locking means 32.

The present invention involves the design of packaging for medical articles such as medical instruments such cutting implements or implants such as orthopedic implants e.g. hip stems, shoulder stems, fixation devices which may be a length of e.g. stainless steel which is used to stabilize fractured bone, or other medical articles which may have abrasive surfaces or surfaces which have coatings or other materials for which contamination or surface removal by abrasion is a concern. In particular the invention may be used for a series of components e.g. shoulder or femoral stem components of various sizes e.g. for artificial joints such as for shoulders or hips, which components have a dimension which does not greatly vary over the size range of the series. The allowed variation in this dimension is such that the package can be designed to just accommodate this dimension for the largest member of the series and yet still accommodate the same dimension of the smallest member of this series without allowing undue motion of this smallest member. The package of the present invention can allow some range of motion to the smallest member of the series so long as this packaged component can still pass the shipping tests to which the manufacturers of medical articles, such as implants, routinely subject such products. This depends on the configuration and weight of the particular component being packaged and tested. In a preferred embodiment the packaging for a given series of stem components will provide a range of clearances for this dimension which ranges from essentially zero to 0.375 inches. The invention also involves the concept of designing such a common package with a clearance which captures this minimally varying dimension but also accommodates a range of sizes in the other dimensions of the medical articles e.g. stem components such as femoral stem components.

It is advantageous to construct the packaging such that the surfaces which contact the surfaces of the stem component have a high abrasion resistance. In this regard, medical articles such as orthopedic implants like stem components are typically constructed with a body portion which has a fairly rough surface to promote adhesion to the bones into which they are implanted. One type of surface with advantageous abrasion resistance is based upon thermoplastic aromatic polyether polyurethane. Deerfield Urethanes, a subsidiary of Bayer, markets suitable thermoplastic aromatic polyether polyurethane films under the trademark Dureflex® with grade PT9400 being particularly suitable. It is also advantageous to use this polyurethane surface to protect to the polished treated surfaces typical of orthopedic implants e.g. femoral stem components such as portions of the angled shaft.

It is also advantageous to construct the packaging out of materials which can be readily thermoformed into packages of suitable rigidity to support the largest component of the series for which the packaging is designed. The typical packaging material for medical implants including femoral stem components has been films of polyethylene terephthalate glycol (PETG) because they have adequate rigidity and mechanical strength and good thermal formability. However, it is desirable to have greater abrasion resistance than this material offers. It is convenient to laminate these films to films of thermoplastic aromatic polyether polyurethane and configure the packaging such that it is the polyurethane surface which faces the surfaces of the medical article e.g. stem component. The laminate is conveniently formed by melt laminating the polyurethane to the PETG. A preferred PETG for this lamination is Eastman's Eastar 6763 PETG resin. The thicknesses for both films should be compatible with both thermoforming the package configuration and providing adequate mechanical strength. A convenient range for the polyurethane is between about 0.01 and 0.025 inches while for the PETG it is between about 0.015 and 0.04 inches.

The packages with which the present invention is concerned can be conveniently designed using computer-aided design (CAD). One approach is to create three dimensional depictions of all the components in a given series such as the size range offered by a given manufacturer e.g. for stem components and then overlay them to determine the location and size of the minimally varying dimension. Commonly, for orthopedic implants such as stem components this is the length of the body portion measured along its outside edge which is a continuation of an outside edge of the lower stem component. Then a package can be designed which provides a clearance which closely approximates minimally varying this dimension and also accommodates the largest size component in the series e.g. the largest femoral component.

Figure 2:
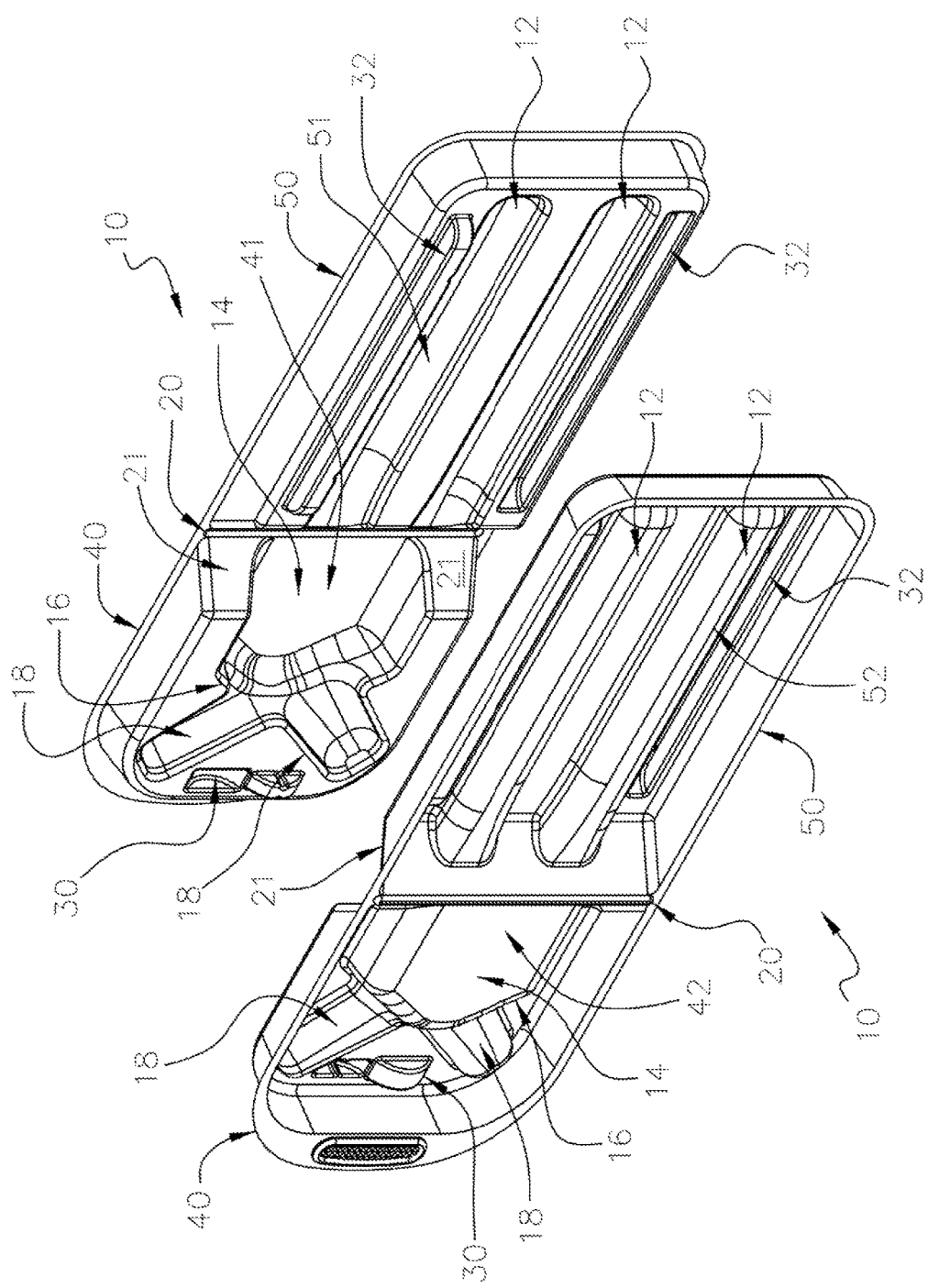
FIG. 2 is a perspective view of the two tray components 10 facing each other such that they can be assembled by forcing them together to form a package for a femoral stem component. In addition to all the elements illustrated in FIG. 1, also shown are the upper tray sections 40 and the lower tray sections 50.
Figure 3:
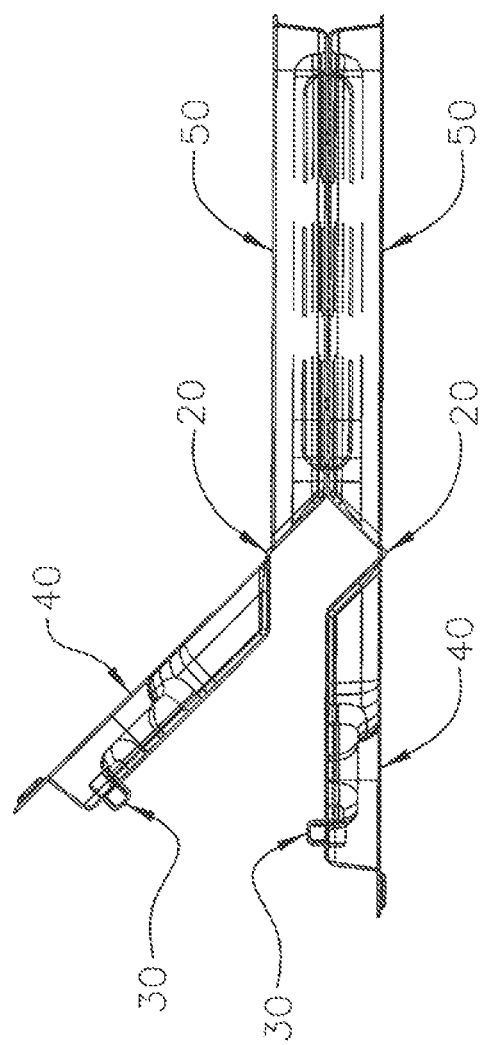
FIG. 3 is a perspective view of the two tray components 10 assembled together showing how the upper tray sections 40 can rotate away from each other via the hinges 20 while the lower tray sections 50 remain affixed to each other.

One approach to the packaging of a series of femoral stem components is illustrated in FIG. 1-3. In this approach two mirror image trays 10 are provided and are joined to each other in a face to face manner as illustrated in FIG. 2. Each tray 10 carries cavities 12, 14 and 18 to accommodate the lower stem, body and angled shaft portions of a stem component. The cavities 12 and 18 are hemi-tubular such that when two trays are joined in a face to face manner they provide tubular cavities to accommodate the somewhat cylindrical elements of the femoral stem component. These cavities 12 and 18 communicate with the cavity 14 which is designed to accommodate the body portion of the stem component via ports 13 and 19, respectively. This cavity 14 is provided with two oblique walls 16 which are at an oblique angle to the main axis of the tray 10 or the cavities 12. Either of the ports 13 and the oblique wall 16 directly opposite this port 13 in the direction of the main axis of the tray component 10 cooperate to capture the minimally varying dimension of the body of the stem component. The port 13 is designed such that the portion of the body adjacent to the lower stem of the series of femoral stem components for which the package is designed is unable to enter this port 13. The distance from this port 13 to this oblique wall 16 approximates the length of the edge of the body portion which is a continuation of an outer edge of lower stem portion of the largest femoral stem component of the series for which the package is designed. Typically femoral stem components carry an edge which proceeds at an oblique angle from the edge of the body portion which is a continuation of an outer edge of lower stem portion to the edge from which the angled shaft projects and it is this edge that the oblique wall 16 approximates. The trays 10 also each carry a hinge 20 which allows thepackage to be partially opened after assembly and two reversible closure means 30 and 32 to facilitate the assembly of the two trays 10 in a face to face manner. Herein, "closure means" or "locking means" is defined as a protrusion and/or a recess disposed in any of the upper and lower trays. allowing the upper and lower trays to snap together.

The illustrated trays 10 are shown as each being symmetric about its main axis because this facilitates their production from a single mold. Any two tray components can then be placed face to face with their cavities facing inward to create an assembled package. However, non-symmetrical tray components could readily be designed to accommodate two different series of femoral stem components. In this case, separate molds would be required for the top and bottom tray components, but the number of sizes that the package could accommodate would be increased. Also, the base and cover or top and bottom trays may be connected by a peripheral hinge alone a top, bottom or side edge.

The package is provided with the ability to be partially opened to allow access to the packaged medical article such as a scalpel, catheter, drug coated implant, or an orthopedic implant e.g. a stem component while still providing some protection and support to this article. The hinges 20 divide each tray component 10 into an upper section or first compartment 40 having an interior surface 41 and exterior surface 42 and a lower section or second compartment 50 having an interior surface 51 and exterior surface 52 as illustrated in FIG. 2-3. The hinges 20 also allow the two upper sections 40 to be rotated away from each other as illustrated in FIG. 3. Thus the connecting hinges 20 (which may be integrally formed with the first and second compartments 40, 50) provide for manual movement of the first compartment 40 relative to the second compartment 50 to rotate a first interior surface 41 of a cover or upper tray from a second interior surface of a base or lower tray. Also, the first compartment of the tray cannot be rotated about an axis of the hinge 20 to a position where the first interior surface 41 of the first compartment covers the second interior surface 51 of the second compartment because of stops formed by hinge walls 21. The provision of separate closure means 30 for the upper tray section 40 and closure means 32 for the lower tray section 50 facilitates the partial opening.

This ability to partially open the package is viewed as a significant benefit to surgical teams e.g. a surgical team implanting an orthopedic article such as a femoral stem component. It allows them clean easy access to a medical article such as a stem component without having it exposed before it needs to be withdrawn from the protective packaging for use such as implantation. It also significantly reduces the risk of dropping the article in the course of removing it from its packaging. To extract a medical article e.g. the stem component from the partially opened package one must have a firm grip on it, while if the two tray components were not hinged for partial opening, but simply stripped from each other there is a chance the stem component would just fall from the packaging.

Working Example

A prototype set of tray components 10 were thermoformed from a melt lamination of 0.01 inch thick Duraflex®PT 9400 aromatic polyether polyurethane onto 0.02 inch thick Eastar® 6763 PETG in such a way that the internal surface facing the contents to be packaged was of the PT9400. Each tray 10 was essentially a rectangle about 10.156" long by 3.875" wide. It had a 0.125" hinge groove which spanned its width located about 6.06" from the short end distal from the angled shaft cavities. Each of the lower stem cavities was about 0.3586" deep and 0.8481" wide with radiused corners. The end of each lower stem cavity flared out to a width of 0.92" at its end proximal to the body cavity 14. The distance from the end of this flare to the oblique wall 16 directly opposite the end of this flare was about 2.0869". Each of the angled shaft cavities 18 had a central axis at an angle of about 47° from the main axis of the tray component 10. The oblique wall 16 deviated from this main axis by about 47°.

Embodiments Of the Invention

1. A rigid synthetic polymer package for medical articles comprising:
   (A) a rigid base having an interior surface and an exterior surface; and
   (B) a cover having at least two compartments including (a) a first compartment having (i) a first interior surface adapted for movement restraining contact with a first portion of a medical article, and (ii) an opposing first exterior surface; and (b) a second compartment having (i) a second interior surface adapted for contact with a second portion of said medical article, and (ii) an opposing second exterior surface; and
   said base and cover having closure means for connected said base and cover together to provide a package for enclosing a medical article having a first portion and connected second portion; said closure means being manually openable for access and removal of said article;
   wherein said first and second compartments of said cover are attached to each other by a connecting hinge adapted for manual movement of said first compartment relative to the second compartment to rotate said first interior surface away from said second interior surface and which cannot be rotated about said connecting hinge to a position where said first interior surface covers said second interior surface.

2. A package, as described in embodiment 1, wherein said base is connected to said cover by a peripheral hinge.

3. A package, as described in embodiment 1 or 2, wherein said base has at least two compartments including (a) a first compartment having (i) a first interior surface adapted for movement restraining contact with a first portion of a medical article, and (ii) an opposing first exterior surface; and (b) a second compartment having (i) a second interior surface adapted for contact with a second portion of said medical article, and (ii) an opposing second exterior surface.

4. A package, as described in embodiment 3, wherein said base and cover are press fit together with said first and second compartments of said base aligned with said first and second compartments of said cover.

5. A package, as described in embodiment 3 or 4, wherein said first and second compartments of said base are attached to each other by a connecting hinge for manual movement of said first compartment relative to the second compartment to rotate said first interior surface away from said second interior surface and said connecting hinge cannot be rotated to a position where said first interior surface covers said second interior surface.

6. A package, as described in embodiments 1-5, wherein said interior surfaces of said base and cover comprise aromatic polyether polyurethane.

7. A package, as described in embodiments 1-6, further comprising a medical article contained within said package and comprising a medical instrument, an implant, an orthopedic implant, a hip joint femoral stem, a shoulder implant, an implant with an abrasion sensitive coating, a cutting tool, or a fixation device for stabilizing a bone fracture.

8. A package, as described in embodiments 1-7, wherein said first compartment of said cover has first and second cavities and said second compartment has a cavity with at least one channel connecting all three cavities.

9. A package, as described in embodiments 1-7, wherein said first compartment of said cover has first and second cavities and said second compartment of said cover has a cavity with at least one channel connecting all three cavities and said base has a first compartment having first and second cavities connected by an integrally formed hinge to a second compartment having a cavity with at least one channel connecting all three cavities; and at least one of said cover channels faces at least one of said base channels; each channel having (i) a second compartment cavity which is a longer hemi-tubular shape generally parallel to a long edge of said package; (ii) a shorter hemi-tubular shaped second cavity of said first compartment which is at an acute angle to a longitudinal axis of said long edge; and said first cavity of said first compartment connects said longer and shorter hemi-tubular cavities and said first cavity has a significantly greater width parallel to a short edge of said package than said longer and shorter hemi-tubular cavities and with a wall in alignment with the longitudinal wall of said longer hemi-tubular cavity closer to the periphery of said package; and
   said closure means adapted to reversibly lock said base and cover in a face to face configuration such that said longer and shorter hemi-tubular cavities form respective longer and shorter tubular cavities; and
   wherein said cavities cooperate to establish a clearance which closely approximates a dimension of the largest member of said series of orthopedic stem components of different sizes.

10. A rigid thermoplastic package component comprising;
    a cover having at least two compartments including (a) a first compartment having (i) a first interior surface adapted for movement restraining contact with a first portion of a medical article, and (ii) an opposing first exterior surface; and (b) a second compartment having (i) a second interior surface adapted for contact with a second portion of said medical article, and (ii) an opposing second exterior surface; and
    said base and cover having closure means for connected said base and cover together to provide a package for enclosing a medical article having a first portion and connected second portion; said closure means being manually openable for access and removal of said article;
    wherein said first and second compartments of said cover are attached to each other by a connecting hinge for manual movement of said first compartment relative to the second compartment to rotate said first interior surface away from said second interior surface and said connecting hinge cannot be rotated to a position where said first interior surface covers said second interior surface.

11. A two piece package thermoformed from a rigid thermoplastic material for the transport and handling of any one of a series of femoral stem components of different sizes for a prosthetic hip joint comprising two facing generally rectangular tray components, with each tray component having
    a. at least one channel which faces an essentially identical channel in the other tray, said channels having;
        i. a longer hemi-tubular section generally parallel the long edge of its tray component;
        ii. a shorter hemi-tubular section at an acute angle to said long edge; and
        iii. a transition section connecting said longer and shorter hemi-tubular sections which provides a cavity of significantly greater width parallel to the short edge of its tray than said longer and shorter hemi-tubular sections and with a wall in alignment with the longitudinal wall of said longer hemi-tubular section closer to the periphery of said tray; and b. means which allows it to be reversibly locked to said other tray component in a face to face configuration such that said longer and shorter hemi-tubular sections form a longer and shorter tubular section, wherein said channels and said transition section cooperate to establish a clearance which closely approximates a dimension of the largest member of said series of femoral stem components of different sizes.

12. The two piece package described in embodiment 11 wherein each of said tray components has a hinge located approximately at the juncture of said longer hemi-tubular section and said transition section which runs parallel to the short edge of said tray component and runs the width of said tray component, thus allowing the portion of said tray component containing said transition section and said shorter hemi-tubular section to rotate out of the plane of said tray component.

13. The two piece package described in embodiment 12 wherein said rotatable portion of each of said tray components carries reversible locking means which functions independently of the locking means which holds the portion of each of said tray components carrying said longer hemi-tubular section to each other.

14. A package described in embodiment 11-12 wherein both of said tray components is fabricated from a laminated thermoplastic such that the surfaces which are adapted to face the femoral components to be packaged are an aromatic polyether polyurethane.

15. A package described in embodiments 14 wherein said aromatic polyether polyurethane is melt laminated to another thermoplastic resin.

16. A package described in embodiment 15 wherein said other thermoplastic resin is polyethylene terephthalate glycol.

The above disclosure is for the purpose of illustrating the present invention and should not be interpreted as limiting the present invention to the particular embodiments described but rather the scope of the present invention should only be limited by the claims which follow and should include those modifications of what is described which would be readily apparent to one skilled in the art.

What is claimed is:

1. A rigid synthetic polymer package for medical articles comprising:
   (A) a rigid base having an interior surface and an exterior surface; and
   (B) a cover having at least two compartments including (a) a first compartment having (i) a first interior surface adapted for movement restraining contact with a first portion of a medical article, and (ii) an opposing first exterior surface; and (b) a second compartment having (i) a second interior surface adapted for contact with a second portion of the medical article, and (ii) an opposing second exterior surface; and
   wherein the base and cover having closure means, and
   wherein the first and second compartments of the cover are attached to each other by a connecting hinge adapted for manual movement of the first compartment relative to the second compartment to rotate the first interior surface away from the second interior surface and which cannot be rotated about the connecting hinge to a position where the first interior surface covers the second interior surface, wherein the first compartment of the cover has first and second cavities and the second compartment of the cover has a third cavity and the base has a first compartment having first and second cavities connected by an integrally formed hinge to a second compartment having a third cavity;
   wherein the third cavity of both the cover and the base is a longer hemi-tubular shape generally parallel to a long edge of the package and the second cavity of both the cover and the base is a shorter hemi-tubular shape at an acute angle to a longitudinal axis of the long edge; and the first cavity of the first compartment of both the cover and the base connects the second and third cavities and the first cavity has a significantly greater width parallel to a short edge of the package than the second and third cavities; and
   wherein the said base and cover are configured face to face such that the longer and shorter hemi-tubular shape cavities form respective longer and shorter tubular shape cavities; and
   wherein the cavities of the cover and the base cooperate to establish a clearance which closely approximates a dimension of the largest member of the series of orthopedic stem components of different sizes.

2. A two piece package thermoformed from a rigid thermoplastic material adapted for the transport and handling of any one of a series of femoral stem components of different sizes for a prosthetic hip joint, the sizes ranging from a smallest component to a largest component, said package comprising two facing generally rectangular tray components, with each tray component having
   a. a longer hemi-tubular cavity generally parallel to a long edge of its tray component and having a width and length;
   b. a shorter hemi-tubular cavity at an acute angle to the long edge, said shorter section having a width and a length; and
   c. a transition cavity in communication with the longer and shorter hemi-tubular sections which has a width parallel to a short edge of its tray, the transition cavity being of significantly greater width than the widths of the longer and shorter hemi-tubular cavities and having a wall in alignment with the longitudinal wall of the longer hemi tubular cavity closer to the periphery of the tray; and
   d. a first closure means; and
   wherein the tray components are configured in a face to face configuration such that the longer and shorter hemi-tubular cavities form a longer and shorter tubular cavity, and
   wherein the tray components cooperate to establish a clearance which closely approximates a dimension of the largest member of the series of femoral stem components of different sizes, and
   wherein each of the tray components has a hinge located approximately at the juncture of the longer hemi-tubular cavity and the transition cavity and the hinge runs parallel to the short edge of the tray component and runs the width of the tray component, thus allowing the portion of the tray component containing the transition cavity and the shorter hemi-tubular cavity to rotate out of the plane of the tray component.

3. The two piece package of claim 2 wherein the first closure means is located on the rotatable portion of each of the tray components and the first closure functions independently of a second closure means which holds the portion of each of the tray components carrying the longer hemi-tubular cavity to each other.

4. The two piece package of claim 2 wherein the rigid thermoplastic material of both of the tray components is comprised of an aromatic polyether polyurethane on the surfaces which are adapted to face the femoral components to be packaged.

5. The two piece package of claim 4 wherein the aromatic polyether polyurethane is melt laminated to another thermoplastic resin.

6. The two piece package of claim 5 wherein the other thermoplastic resin is polyethylene terephthalate glycol.

\* \* \* \* \*